United States Patent [19]

Stephenson et al.

[11] 4,404,367
[45] Sep. 13, 1983

[54] GLUCOSUBSTITUENTED DITERPENOID SWEETENERS

[75] Inventors: Rebecca A. G. Stephenson, Redwood City; Paul S. Dietrich, Mountain View; Grant E. DuBois, Palo Alto; Leonard A. Bunes, San Carlos, all of Calif.

[73] Assignee: Dynapol, Palo Alto, Calif.

[21] Appl. No.: 296,566

[22] Filed: Aug. 26, 1981

[51] Int. Cl.³ .................. C07H 15/24; A23L 1/236
[52] U.S. Cl. ........................ 536/18.1; 426/658; 426/548
[58] Field of Search ............ 426/548, 658; 536/4, 536/18.1

[56] References Cited

U.S. PATENT DOCUMENTS 3,876,816  4/1975  Zaffaroni ........................... 426/548
4,082,858  4/1978  Morita et al. ................... 426/658 X
4,226,804  10/1980 DuBois et al. ................. 426/548 X
4,332,830  6/1982  DuBois ............................. 426/548

Primary Examiner—Joseph M. Golian
Attorney, Agent, or Firm—Burns, Doane, Swecker & Mathis

[57] ABSTRACT

Glucosubstituented diterpenoid compounds analogous to stevioside, rebaudosides C and A, steviolmonoside and steviolbioside but having their gluco units substituted with simple monoglycosidic polar groups and optionally having their $C_{19}$ carboxyls as simple esters are disclosed. These materials are sweet and do not degrade under mammalian GI tract conditions.

24 Claims, No Drawings

GLUCOSUBSTITUENTED DITERPENOID SWEETENERS

BACKGROUND OF THE INVENTION

1. Field of the Invention

This invention relates to chemical analogs of the sweet glycosides, stevioside and rebaudioside A, which are themselves sweet and useful as sweeteners and which do not degrade under conditions of use to form physiologically undesirable steviol as do stevioside and rebaudioside A.

2. The Prior Art

The leaves of the Paraguayan shrub *Stevia rebaudiana* Bertoni have long been known to be sweet. Several sweet crystalline glycosides have been isolated from these leaves. The principal compound is named stevioside. The secondary compound differs from stevioside in the identity of its saccharide substituent and is known as rebaudioside A. These materials have the structures shown in general formulae I and II, respectively.

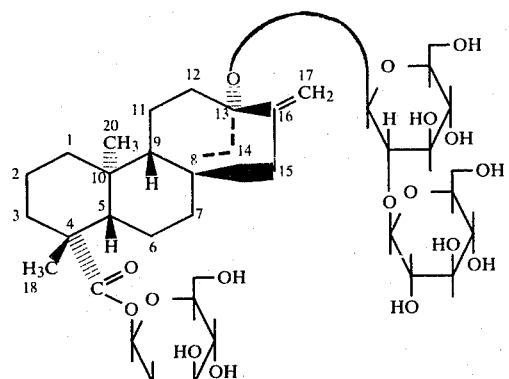

These compounds have been identified as possible sweeteners as they provide a relatively sucrose-like intense sweetness. A threshold question with these materials concerns their safety. In 1966, P. V. Vignais and coworkers reported the results of a study concerned with elucidation of the mode of action of the respiratory toxin, atractyligenin. Included in their study were several compounds of related structure including steviol (III), the aglycone of stevioside and rebaudioside A.

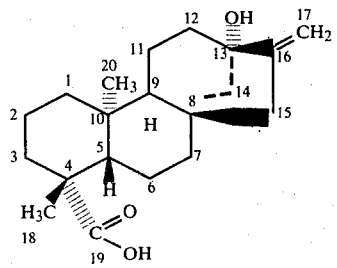

Surprisingly, in cell mitochrondria, steviol was found to be an even more potent inhibitor of ATP synthetase then atractyligenin. (*Biochim. Biophys. Acta,* 118, 465–483 (1966)). In addition, steviol is reported to exhibit antiandrogenic effects (Dorfman, R. I., et al., *Endocrinology,* 67, 282–285 (1965)). Clearly, if stevioside and rebaudioside A were converted to steviol in vivo, significant toxicity may be expected. Recent results suggest the likelihood that both materials would be largely converted to steviol in vivo, and further that the steviol thus produced would subsequently be completely absorbed through the gastrointestinal tract wall. (R. Wingard, J. Dale, J. Brown, R. Hale, *Experientia,* 36, 519, (1980)) Thus, as a result of a combination of the Vignais and Wingard work, it may be concluded that, with widespread use, stevioside or rebaudioside A may be expected to exhibit significant acute toxicity. If, however, their metabolism to steviol could be prevented, that is if potently sweet analogs could be developed which were not degraded to steviol, safety for use in foods would be anticipated.

In copending U.S. patent application Ser. Nos. 272,799 now U.S. Pat. No. 4,353,889 and 272,798 of Grant E. DuBois, it is shown that the glucose attached to the $C_{19}$ carboxyls of stevioside and rebaudioside A can be replaced with a polar nonglycosidic group while retaining sweetness.

Also in concurrently filed and now pending U.S. patent application Ser. No. 296,568 it is disclosed that sweet analogs of steviolmonoside can be formed.

STATEMENT OF THE INVENTION

A family of new chemical analogs of stevioside and rebaudioside A has now been discovered. These materials are useful as sweeteners and unexpectedly have the property of being stable to mammalian gastrointestinal tract conditions and not generating steviol in vivo. We have found that the metabolism of these glycosides to steviol is an enzyme mediated process. Glycosidases in the mammalian gut cleave the three (stevioside) or four (rebaudioside A) glucoses. Similarly, glycosidases can cleave the one, two or three glucoses attached to the C-13 oxygen in the steviol-13,19-bioside, stevioside and rebaudioside A analogs shown in the above-noted copending patent applications. This is notwithstanding the fact that these compounds have a simple C-19 carboxyl substituent that prevents the generation of steviol per se.

We've further discovered that we can chemically disguise these glucoses so that the glycosidases "don't recognize" them. Interestingly, while the modification prevents enzyme attack, the potent sweetness observed for the parent compounds is retained in the "disguised" compounds.

We have also found that modifiers attached to the glucoses can raise the compounds' molecular volume and weight to a level that the compounds are not absorbable from the gut. Such a finding is consistent with the prior generic invention of nonabsorbable sweeteners made by Alejandro Zaffaroni and embodied in his U.S. Pat. No. 3,876,816.

In the compounds of the invention, at least one hydroxyl hydrogen on each of the glucose units is covalently substituted by a simple noncarbohydrate polar organic group R'.

We refer to these new compounds as glucosubstituented steviosides, glucosubstituented rebaudioside As, glucosubstituented steviolbioside esters, glucosubstituented rebaudioside C esters and glucosubstituented steviolmonoside esters.

In another aspect, this invention involves the use of these new compounds as sweeteners for comestibles wherein they are admixed with said comestibles.

DETAILED DESCRIPTION OF THE INVENTION

The Compounds

In this Description of the Invention reference will be made to a variety of related diterpenoid compounds. These compounds include:

Stevioside—the natural product shown in general formula I

Rebaudioside A—the natural product shown in general formula II

Steviol—the aglycone of rebaudioside A and stevioside shown in general formula III Steviolbioside—the base hydrolysis product of stevioside having the structure shown in general formula IV

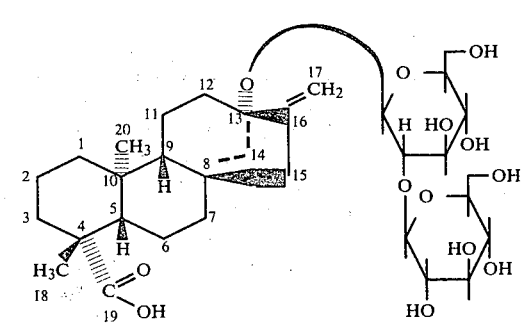

Steviol—13,19-bioside-the product of enzyme mediated removal of the terminal glucose of the stevioside sophorose moiety.

Rebaudioside C—the base hydrolysis product of rebaudioside A having the structure shown in general formula V

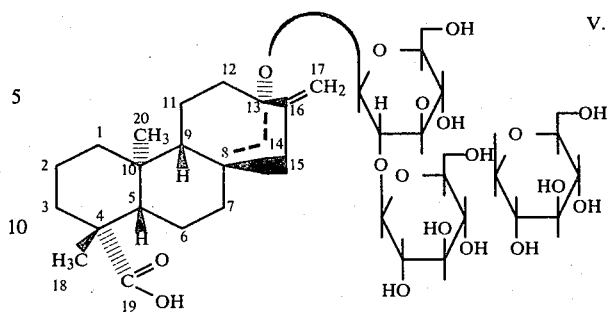

Steviolmonoside—the base hydrolysis product of Steviol-13,19-bioside. This material is shown in general formula VI.

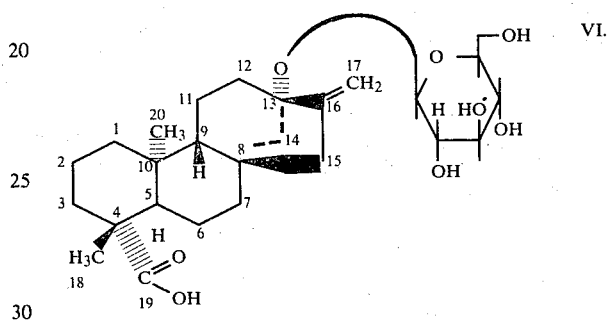

Glucosubstituented stevioside—a compound of general formula I wherein at least one hydroxyl hydrogen on each glucose ring is replaced by R', the same or different simple polar organic group.

Glucosubstituented rebaudioside A—A compound of general formula II wherein at least one hydroxyl hydrogen on each glucose ring is replaced by R', the same or different simple polar organic group.

Glucosubstitutented steviolbioside ester—a compound of general formula IV wherein the C-19 carboxyl hydrogen is replaced by a simple polar organic group and wherein at least one hydroxy hydrogen on each glucose ring is replaced by R', the same or different simple polar organic group. If the C-19 carboxyl hydroxyl is present, this would be glucosubstituented steviolbioside.

Glucosubstitutented rebaudioside C ester—a compound of general formula V wherein the C-19 carboxyl hydrogen is replaced by a simple polar organic group and wherein at least one hydroxy hydrogen on each glucose ring is replaced by R', the same or different simple polar organic group. If the C-19 carboxyl hydroxyl is present, this would be glucosubstituented rebaudioside C.

Glucosubstituented steviolmonoside ester—A compound of general formula VI wherein the C-19 carboxyl hydrogen is replaced by a simple polar organic group and wherein at least one hydroxy hydrogen on each glucose ring is replaced by R', the same or different simple polar organic group. See above for when C-19 carboxyl hydroxyl is present.

As shown in the above-mentioned patent applications, the ester compounds of this invention also differ structurally from the art known natural products or steviolmonoside in the nature of the "R" substituent on the C-19 oxygen atom. R is hydrogen or a physiologically acceptable noncarbohydrate polar organic group.

R has the additional constraint that it should not have oxygen substitution on its α-carbon, that is, it should be α-carbon oxygen free as such substitution in this position is equivalent to hemiacetal or acetal functionality which are unstable in vivo and could lead to formation of steviol. The α-carbon can be a substituted with carboxy, sulfo, phospho, and similar polar groups, however.

R and R' may preferably be selected from among 1 to 10 carbon atom physiologically acceptable noncarbohydrate polar organic groups. They may be the same or different. Preferably, R and R' have from 2 to about 5 carbon atoms. Of necessity, these polar groups will include atoms beyond carbon and hydrogen such as the heteroatoms oxygen, sulfur, nitrogen and phosphorous. These heteroatoms may form anionic or cationic or zwitterionic polar moieties including sulfonate, sulfamate, carboxylate and phosphonate anions, hydroxyls, ammonium cations, and combinations thereof. These polar groups are accompanied by physiologically acceptable counterions. Representative R and R' groups include the materials listed in Table I. Table I also lists precursors or precursor sequences which can be used to insert these R and R' groups as will be set forth herein as Preparative Methods.

salts; glucocarboxymethylated rebaudioside C, potassium and sodium slts; glucocarboxymethylated steviolbioside, potassium and sodium salts; glucocarboxymethylated steviolmonoside potassium and sodium salts.

PREPARATIVE METHODS

The compounds of the invention can be prepared as follows:

The stevioside or rebaudioside A analogs start with the natural products, stevioside or rebaudioside A, and react it with the R' addition agent in the presence of a strong base.

The steviolbioside or rebaudioside C analogs can be prepared from the respective natural products by the general preparative scheme of saponifying stevioside or rebaudioside A to produce steviolbioside or rebaudioside C and then reacting steviolbioside or rebaudioside C with an "R'-addition" reagent.

In the case of steviolmonoside, the same procedure is employed with the addition that the terminal glucose of the C-13 sophorose moiety is first enzymatically removed from stevioside to yield steviol-13,19-bioside.

More particularly, the conversion of stevioside to steviol-13,19-bioside is carried out according to the enzymatic process suggested by Kaneda, N; Kasai, R;

TABLE I

| R or R' GROUP | Precursors |
|---|---|
| 1-5 carbon alkyl terminal sulfonates: | $Br-(CH_2)_n-SO_3^-M^+$ |
| $-(CH_2)_n-SO_3^-M^+*$ | 1,3-Propane sultone |
| n = 1-5, preferably 2-5, more preferably 3 or 4 and most preferably 3 | 1,4-Butane sultone |
| 1-5 carbon alkyl polysulfonates (preferably 2-5 carbons) | $Br-(CH_2)_n-CH(SO_3^-M^+)_2$ |
| $-CH_2-CH-(SO_3^-M^+)_2$ | |
| $-(CH_2)_2-CH-(SO_3^-M^+)_2$ | Etc. |
| 1-5 carbon alkyl terminal carboxylates | $Br-(CH_2)_n-COO^-M^+$ |
| $-(CH_2)_n-COO^-M^+$ | |
| n = 1-5 preferably 1-3 | |
| 1-5 carbon alkyl polycarboxylates | $Br-CH-(COO^-M^+)-(CH_2)_2-COO^-M^+$ |
| $-CH(COO^-M^+)-(CH_2)_2-COO^-M^+$ | |
| Etc. | |
| 1-5 carbon alkyl terminal phosphonates | $Br-(CH_2)_n-PO_3=(M^+)_2$ |
| $-(CH_2)_n-PO_3H^-M^+$ | |
| n = 1-5, preferably 2-4 | |

*$M^+$ = physiologically acceptable alkali metal or alkaline earth metal cation, particularly $Na^+$, $K^+$, $Mg^{++}$ or $Ca^{++}$ These R and R' groups are merely representative. For example, straight chain materials have been shown but branched materials can be used as well. Other equivalent organic groups may be substituted so long as they are noncarbohydrate and polar. In general, it is preferred to have R and R' the same.

The following compounds of the invention are preferred:
  rebaudioside C,
  steviolbioside, and
  steviolmonoside, each having a 1 to 5 carbon alkyl terminal sulfonate as both R and R' or having a 1 to 5 carbon alkyl terminal carboxylate as R' and hydrogen as R. Preferred alkyl sulfonates include $-(CH_2)_3-SO_3^-K^+$ and $-(CH_2)_3-SO_3^-Na^+$, while preferred carboxyalkyls include $-(CH_2)-COO^-K^+$ and $-(CH_2)-COO^-Na^+$. These most preferred materials are named glucosulfopropylated rebaudioside C, sulfopropyl ester, potassium and sodium salts; steviolbioside, sulfopropyl ester, potassium and sodium salts; and steviolmonoside, sulfopropyl ester, potassium and sodium Yamasaki, K; and Tanaka, O; in *Chem. Pharm. Bull.* 25 2466-2467 (1977) using Takadiastase Y enzyme or its equivalent. This disclosure is incorporated by reference. Other suitable enzymes include naringinase, various α-amylases and mixed glycosidases from sources such as Cheronalampas, Turbo cornutus and Helix pomatia. The enzyme reaction is carried out by dissolving the stevioside and about an equal weight—e.g. 0.25 to 5.0 times, preferably 0.5 to 3 times the weight of stevioside—of enzyme in a suitable sterile liquid medium or broth. Suitable broths include sterile aqueous mildly acidic broths and especially buffered citric acid such as buffered to pH 4-5 with an alkali metal hydrogen phosphate. The concentration of stevioside is about 1 mg per ml, say from 0.2 to 20 mg/ml. Moderate temperatures are employed for the incubation with temperatures from 25° to 45° C., being preferred. The reaction is complete in a few (3-10) days. Usually one monitors its progress with thin layer chromatography or a like analytical method and continues the reaction to completion.

The saponification of stevioside, rebaudioside A or steviol-13,19-bioside is carried out by reacting the natural products or the bioside with a molar excess (at least 5 equivalents) of a strong base, especially aqueous or alkanolic or mixed aqueous-alkanolic KOH or NaOH and particularly aqueous and/or methanolic KOH, at elevated temperatures such as from 50° C. to 150° C., preferably 60°-100° C. for a time adequate to effect essentially complete saponification. An especially preferred reaction uses 40-80% methanol as cosolvent as this gives an easily filtrable granular product. At atmospheric pressure this reaction is best carried out at about 65° C., the boiling point of methanol. The concentration of the base is generally from about 1%wt to about 20% wt. The time required is in the range of from 0.1 hours to 3 and would depend upon the temperature employed. At higher temperatures, say 100°-150° C., times from 0.1 to 1 hour are preferred. At lower temperatures, say 50°-100° C., times from 1 to 3 hours are preferred.

Following saponification, the reaction medium is generally neutralized, such as with mineral acid, and the steviolbioside, steviolmonoside or rebaudioside C is recovered. This recovery can be effected by crystallization, brought about by cooling or removal of solvent. The steviolmonoside, steviolbioside or rebaudioside C can be purified by recrystallization, column chromatography or a like process at this point. Such a purification is generally performed.

The insertion of the R' groups into the glucose rings is performed by contacting the proper diterpenoid glycoside with the appropriate R' addition agent in liquid phase in the presence of a strong base. This will effect essentially instantaneous addition.

The particular "R'-addition" agent employed of course depends upon the "R'" group sought to be added. A list of exemplary R'-addition agents is provided in Table I. In general, any reagent that will displace a hydroxyl hydrogen on the glucose units with an R', can be used. About 3 equivalents of R'-addition agent is used per equivalent of R' addition desired. A strong base, for example an alkali metal dimsylate such as the reaction product of sodium or potassium hydride with DMSO is present in an amount about equal to the equivalents of R'-addition agent. Usually, one equivalent of base is followed by one equivalent of R'-addition agent. This process is repeated until TLC shows complete reaction. This reaction may be conducted under dry argon at low to moderate temperatures (15° C. to 30° C., preferably 15°-25° C.) for a brief period such as from 1 to 10 minutes with agitation. Longer time may be used but is not seen to offer advantages. This reaction is carried out in liquid phase in an aprotic reaction medium, such as dimethylsulfoxide and the like.

Following reaction with the R'-addition agent and neutralization with aqueous acid, the product is recovered such as by concentration in vacuo followed by recrystallization. Other equivalent recovery and purification processes may be employed.

For the cases of steviolmonoside, steviolbioside, and rebaudioside C, the R'-addition reaction may also result in addition to the C-19 carboxyl moiety. The success of this latter addition is dependent on alkylating agent reactivity, potent alkylating agents such as propanesultone resulting in substitution while poorer alkylating agents such as sodium chloroacetate giving no substitution.

This process will add an R' unit to each hydroxyl unit on each glucose ring. If it is desired, as is preferred, to have less than full substitution it is generally preferred to protect some of the hydroxyls and add R's to the others and then remove the protecting groups. Classis carbohydrate chemistry techniques work perfectly for this. For example, benzaldehyde dimethylacetal in DMF with perchloric acid catalyst can block the C-4 and C-6 hydroxyls on each glucose unit and can be simply removed under mild hydrolytic conditions. This process is shown in C. Piantadosi, C. E. Anderson, E. A. Brecht, C. L. Yarbo, *J.Amer.Chem.Soc.* 80, 6613C, (1958), which is incorporated herein by reference.

These preparative conditions are merely representative. Other equivalent routes may be employed if desired.

STABILITY OF COMPOUNDS

An important property of these analogs is their stability and resistance to conversion to steviol at the conditions of the mammalian gastrointestinal tract. This property is demonstrated in vitro by anaerobically incubating the compounds of the invention with fresh rat cecal contents for three days at 37° C. At these conditions, no degradation to steviol occurs to a limit of detection of 0.13%. In direct contrast, as reported in the *Experientia* paper of Wingard, et al., noted above, stevioside and rebaudioside A themselves and presumably steviolmonoside undergo major degradation to steviol.

It is also important to note that when the glucose units are substituented according to this invention so as not to be cleavable, the compounds of the invention have molecular weights in the range of 700-1200 daltons. All of these are large enough to be poorly absorbable from the gut while the larger are big enough to be essentially nonabsorable. As pointed out by A. Zaffaroni in U.S. Pat. No. 3,876,816, when a compound is nonabsorbable from the gut it does not enter the body. Thus, it cannot pose systemic toxicity problems.

USE OF THE COMPOUNDS

The compounds of this invention are useful as sweeteners for comestibles. In this application, they are simply admixed with the comestible by art-known means in dry form or as solutions, preferably in water. They are, advantageously, soluble in water at usual use levels. Representative comestibles include beverages such as sodas, coffee, lemonade, wine and the like; edibles such as gelatin desserts, candy, gum, cakes, cereals and the like, personal products such as mouth wash and toothpaste as well as pharmaceuticals such as cough syrups, and flavored pills.

The compounds of this invention are about 30 to 200 times as sweet as sucrose on a weight basis. Accordingly, the amounts to be employed may be determined by factoring usual sucrose use levels by this 30-200 value. Thus, for example, a soft drink might be sweetened by adding 0.04 to 0.40% by weight of the present compounds. Mixtures of these materials alone or with known other sweeteners (sucrose, saccharin or the like) may also be advantageously employed.

The invention will be further described by the following Examples. These are provided solely to illustrate the invention and are not to be construed as limiting its scope.

PREPARATION OF STARTING MATERIALS

A. Stevioside (Morita Chem. Co., Osaka, Japan)

B. Rebaudioside A isolated from Steviron F (17% rebaudioside A) (Morita Chem. Co., Osaka, Japan) by silica gel chromatography (CHCl₃—MeOH—H₂O) followed by recrysallization from ethanol.

C. Steviolmonoside

According to the procedure of Tanaka et al, supra., a 4.604 g sample of the recrystallized stevioside was incubated for 8 days with 4.605 g of Takadiastase Y (Sanzyme R) in 460 ml of a pH 4.05 broth made up of 61 volume % 0.1 M citric acid and 39 volume % 0.2 M Na₂HPO₄ at 37° C. Periodic samples were taken and anaylzed by thin layer chromatography for disappearance of starting material and appearance of new products. During incubation a large amount of white precipitate formed. At the end of the incubation, the slurry was diluted to 800 ml with distilled water. This mixture was then extracted thrice with n-butanol. The extracts were then evaporated and the solid dissolved in methanol and recrystallized. The major component of the recrystallized product was steviol-13,19-bioside (Compound II). The recrystallized product of this and a duplicate run were then chromatographed over 500 g of silica gel (60-200 mesh) eluting with CHCl₃—CH₃OH—H₂O mixtures. Combination of pure fractions gave 5.14 g (70%) of steviol-13,19-bioside.

Steviol-13,19-bioside (4.33 g 5.5 mmol) was added to 95 ml of 10% NaOH and 95 ml of methanol in a 500 ml flask. After flushing with argon, the mixture was heated to reflux. After 1.5 hrs., the reaction mixture was cooled to 5° C., and brought to pH 3.3 with 50% H₂SO₄. A solid precipitate formed. This mixture was extracted with ethyl acetate (4×50 ml), the combined portions of which were dried over MgSO₄ and concentrated to dryness to yield a colorless solid. This solid was recrystallized from methyl ethyl ketone/methanol. The resulting tan-white prisms were washed with neat methyl ethyl ketone and vacuum dried to yield 1.156 g of a product which by TLC and HPLC analysis was found to be homogeneous.

D. Steviolbioside

According to the procedure of H. B. Wood, R. Allerton, H. W. Diehl, and H. G. Fletcher (J. Org. Chem. 20, 875-883 (1955)), 771 mg (0.96 mmole) of stevioside was saponified with 25 mls 10% KOH at reflux for 1 hour. After cooling, the reaction mixture was acidified to pH 3 with 10% H₂SO₄. After further ice-bath cooling for several hours, filtration yielded a white solid. Recrystallization from methanol yielded 560 mg (91%) of steviolbioside as a white flocculent solid.

E. Rebaudioside C

Rebaudioside A (0.2 mmol, 183 mg) was transferred to a 15 ml flask. Four ml each of 10% KOH and methanol were added and the resultant mixture heated to yield a homogeneous solution which was refluxed for 1.5 hours. Reaction was then judged complete by TLC analysis. After cooling to 0°; the reaction mixture was acidified to pH 3 with 10% H₂SO₄. The resultant mixture was then concentrated to dryness and the residue recrystallized from water to give 150 mg (99%) of pure rebaudioside C.

F. Potassium Dimsylate

Potassium hydride was dissolved in DMSO to give a standard solution containing 0.50 mmol per ml of potassium dimsylate. This preparation can be repeated with sodium hydride to yield a sodium dimsylate solution.

EXAMPLE I

A.

Preparation of Steviolbioside, 4',6',4",6"-bisbenzylidene acetal (SB-BBA)

To a solution of 1.29 g (2.00 mmols) of steviolbioside and 1.52 g (10.0 mmols) of benzaldehyde, dimethyl acetal in 20 mls dry DMF was added one drop of 70% HClO₄. The resultant reaction mixture was stirred at 45° C. under dry argon for 24 h at which point, 1.52 g (10.0 mmols) additional benzaldehyde, dimethyl acetal was added and heating continued for 8 h. At this point, TLC (Silica Gel F-254 CHCl₃—MeOH—H₂O: 15-5-0.5) showed all the steviolbioside (Rf=0.14), and steviolbioside, monobenzylidene derivatives (Rf=0.41, 0.44) to have been consumed to produce only SB-BBA (Rf=0.62). The reaction mixture was then poured into 200 ml H₂O and extracted with ether (3×50 ml), the combined portions of which were washed with H₂O (6×50 ml), dried over MgSO₄ and concentrated to yield 1.53 g of a white solid. This product was purified by chromatography on a Chromatotron rotary preparative chromatography system (4 mm Silica Gel G rotor; CHCl₃-MeOH) to yield 1.26 g (77%) of chromatographically pure SB-BBA. Recrystallization (H₂O-MeOH) yielded 1.01 g of hygroscopic tiny clusters: mp 195°-205° C.; HPLC: (30 cm C-18 on μ-Bondapak; 10-40%. MeCN in 0.005 M KH₂PO₄; 2.0 ml/min; 15 min linear program; 254 nm) $t_R$=15.3 min. IR λKBrMax 2.92 (O—H), 5.83 (C=O), 6.90, 7.24, 8.52, 9.22, 13.2, 14.3; H-NMR $_{CDCl_3}{}^{TMS}$ 0.91 (3Hs, C-20-CH₃), 1.12 (3Hs, 18-CH₃), 1.1-2.3 (18 m, C-1-C-14 CH₂,CH), 3.0-4.3 (14Hm, C-15CH₂, C-2'-C-6', C-2"-C-6"CH₂, CH), 4.63 (1Hd, J=8 Hz, C-17H), 4.79 (1Hd, J=8 Hz, C-17H), 4.82 (1H, brs, OH), 5.07 (1H brs,O—H), 5.36 (1H brs, O—H), 5.5-6.0 (4Hm,C-1',C-1",C-H,PhCH), 7.39 (10Hs,PhH), 11.96 (1H brs, COOH) ppm; C-NMR $\delta_{CDCl_3}{}^{TMS}$ 152.6 (C-16), 104.8 (C-17) ppm; Anal.Calc. for C₄₆H₅₈O₃.H₂O: C, 66.01; H, 7.23; Found: C, 66.11; H, 7.13.

B.

Preparation of 3'-0,2"-0,3"-0-Tris-sulfopropyl Steviolbioside, Sulfopropyl ester, Tetrasodium Salt (TSSB).

To a solution of 1.06 g (1.24 mmols) of steviolbioside, 4',6',4",6"-bisbenzylidene acetal in 10 mls dry DMSO in a 100 ml one necked flask was added dropwise while stirring at ambient temperature under dry argon 9.92 ml of 0.50 M potassium dimsylate-DMSO solution (4.96 mmols), followed immediately by 9.92 ml of 0.50 M 1,3-propane sultone-DMSO solution. This process was repeated two times additionally at which point TLC (Silica gel F-254; CHCl₃—CH₃OH-H₂O: 15-10-2) and HPLC (30 cm C-18 on μ-Bondapak column; 10-40% MeCN in 0.005 MKH₂PO₄; 2.0 ml/min;15 min linear gradient; 200 nm) analyses of a reaction aliquot indicated the reaction to have proceeded to completion to give one polar product (Rf=0.21; $t_R$=12.4 min). The reaction mixture was then diluted with an equal volume of water and the resultant aqueous mixture neutralized with 10% HCl. This solution was then concentrated in vacuo to give a tan solid which on recrystallization from 99:1 CH₃OH-H₂O yielded 1.28 g (72%) of 3'-0,2"-0,3"-0-tris-sulfopropyl steviolbioside, 4',6',4",6"-bisbenzylidene acetal, sulfopropylester, tetrapotassium salt as off-white clusters. Treatment of 1.20 g (0.82 mmol) of this compound under mild acidic conditions (50 ml pH 2 $H_2SO_4$, 20°, 18h) resulted in quantitative deprotection, as shown by HPLC analysis of a reaction aliquot to yield one polar product ($t_R=9.1$ min). The pH was adjusted to 5 with a few drops 5% NaOH after which the resultant mixture was concentrated to dryness. The residue was triturated with several portions of ether to remove benzaldehyde after which it was heated (50°, 18 h) with 12 mmol 1.00 M KOH to ensure hydrolysis of any excess propane sultone. This solution was neutralized with 10% HCl and was then passed through a column of 400 g BioRad AGMP50 (Na form). The resultant solution of sodium salts was concentrated to approximately 5 ml and was then desalted by slow passage through a column of 40 cc of BioRad AG 11 A8 ion retardation resin. The product thus obtained Product IA was then recrystallized ($CH_3OH$-ether) to yield 0.733 g (73%) of TSSB as off-white clusters: mp 109.5°–112° (dec); IR $\lambda_{max}^{KBR}$ 2.92(OH), 5.86(C=O), 6.10(C=C), 8.35(S=O), 9.60(S=O)$\mu$.

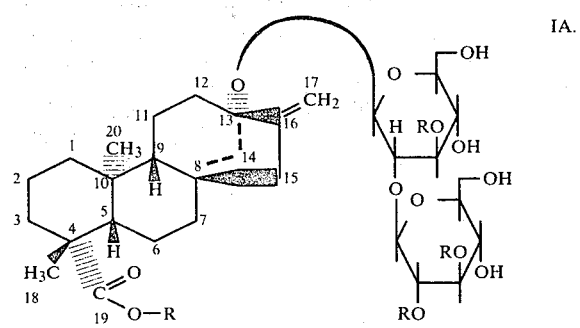

IA.

C.

A 5000 ppm solution of the compound IA was made up in water and tasted by a group of volunteers. They reported a very intense pure sweet taste which, by comparison to other more completely evaluated sweeteners, was estimated to be about 30 times as potent as sucrose on a weight basis.

D.

Compound IA is incubated anaerobically for three days at 37° C. with 5% fresh rat cecal contents at concentrations of 0.25, 0.5, and 1.0 mg/ml, in sterile Krebs-Ringer 0.25 M phosphate buffer (pH 7.4) containing 0.25 mg/ml dithiothreitol and 0.25 mg/ml α-D-glucose. TLC [silica gel F-254; $CHCl_3:CH_3OH:H_2O$ (15:10:2)] and HPLC [30 cm C-18 on $\mu$-Bondapak; 15 min linear gradient of 10–40% $CH_3CN$ in 0.005 M $KH_2PO_4$ (pH 3.45); 200 nm] analysis shows that the compound (Rf=0.21, $t_R=12.4$ min) is not consumed. No steviol ($R_f=0.95$; $t_R=31.3$ min) or steviol, sulfopropylester, sodium salt (Rf=0.63, $t_R=16.3$ min) are detected.

E.

Use in Comestibles

Based on the results of Part C, one can employ the compound IA as a sweetener for comestibles. In exemplary uses 0.30% by weight of the compound is dissolved in an unsweetened cola beverage, a like concentration of the compound is added to an unsweetened lemonade and to coffee. In each case, sweetness is imparted. In two other cases, 0.15% by weight is added to coffee along with 0.02% by weight of saccharin and 3% by weight of sucrose, respectively. Again, sweetness is imparted by the compound of Part B.

EXAMPLE II

A solution of compound IA of Example I is passed through an ion exchange column charged with $K^+$. This forms the 3-sulfopropyl ester, potassium salt. This product was sweet. Similarly $\frac{1}{2} Ca^{++}$ or $\frac{1}{2} Mg^{++}$ could replace $K^+$. When this material is evaluated, as in Parts C, D and E of Example I, it exhibits the same advantageous properties observed with the material of Example I.

EXAMPLE III

A.

Preparation of 3'-0,2''-0,3''-0-Tris-carboxymethyl Steviolbioside, (TCSB), Trisodium Salt.

This procedure was identical to Example I, part B except that a 0.50 M solution-suspension of sodium chloroacetate-DMSO was used in place of the propane sultone solution and that 3 mmol portions of potassium dimsylate and alkylating agent were used rather than 4 mmol portions. TLC and HPLC (as in Example I, part B, except that 10–40% MeCN in 0.005 M $K_2HPO_4$ buffer (pH 7) was used as eluant showed the reaction to have proceeded cleanly to one polar product (Rf=0.43, $t_R=14.2$ min). The reaction mixture was then diluted with an equal volume of water and acidified to pH 5 with 10% HCl thus resulting in product precipitation. Filtration on a Buchner funnel yielded 1.02 g (80%) of 3'-0,2''-0,3''-0-tris-carboxymethyl steviolbioside, 4',6',4'',6''-bisbenzylidene acetal as a pure white solid. This compound was deprotected as in Example I, part B (omitting the treatment with 12 mmol KOH and later steps) to give after recrystallization from $CH_3OH$-ether 0.59 g (75%) of TCSB as an off-white powder. Treatment with 3.0 equivalents of 1.00 M NaOH followed by lyophilization gave a quantitative yield of TCSB, trisodium salt.

B.

When tasted, this material is observed to be sweet, like the material of Example I.

EXAMPLE IV

The preparation of Example I is repeated using rebaudioside C as starting material.

The blocking of two OH's per glucose is carried out so that the rebaudioside C structure contains 4 free glucose hydroxyl moieties. Thus a substitution of five oxygen atoms with propanesultone as R and R' addition agent is carried out. Following removal of the blocking groups, the desired product is isolated and purified.

EXAMPLE V

The preparation of Example I was repeated using steviolmonoside as starting material. After blocking two OH's on the single glucose unit, 3 equivalents of replaceable hydroxyl remained. Thus, a substitution with propane sultone as the R and R' addition agent was carried out. Following removal of the blocking groups, the desired product was isolated and purified.

EXAMPLE VI

The preparation of Example I is repeated three times using steviolbioside, stevioside and rebaudioside A as starting materials. No blocking is carried out so that steviolbioside contains 8, stevioside 11, and rebaudioside A 14 substitutable hydroxyl groups. Appropriate amounts of potassium dimsylate and propane sultone are employed and the desired products are isolated and purified.

What is claimed is:

1. A rebaudioside C analog compound based on the structure

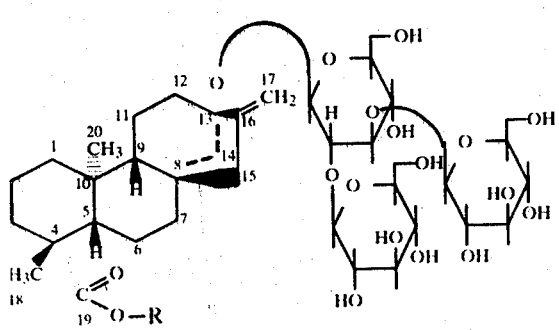

wherein R is hydrogen or a physiologically acceptable noncarbohydrate α-carbon oxygen free 1 to 10 carbon atom polar organic group and each of the glucose rings has at least one of its OH units substituented to OR' wherein R' is a covalently bound physiologically acceptable noncarbohydrate polar organic group.

2. The compound of claim 1 where R is said polar organic group.

3. The compound of claim 2 wherein R and R' each contains one or more polar moiety selected from sulfonate, sulfamate, carboxylate, and phosphonate anions, ammonium cations and hydroxyl groups.

4. The compound of claim 3 wherein R and R' are each a 1 to 5 carbon inclusive alkyl terminal sulfonate salt.

5. The compound of claim 4 wherein R and R' are the same and of the formula

—(CH$_2$)$_n$—SO$_3^-$M$^+$ wherein n is an integer from 2 to 5 inclusive and M$^+$ is a physiologically acceptable alkaline earth metal cation or alkali metal cation.

6. The compound of claim 5 wherein n is 3 and M$^+$ is Na$^+$ or K$^+$.

7. The compound of claim 1 where R is hydrogen and R' is a 1 to 5 carbon atom alkylcarboxylate.

8. The compound of claim 7 wherein R' is a carboxymethyl group.

9. A steviolbioside analog compound based on the structure

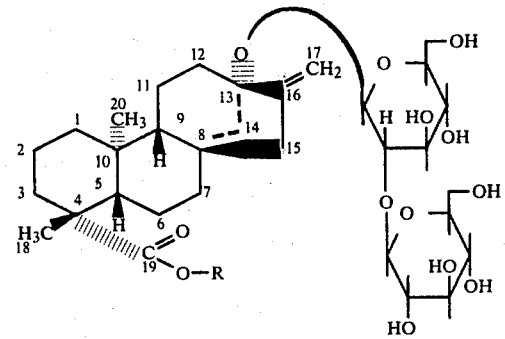

wherein R is hydrogen or a physiologically acceptable noncarbohydrate α-carbon oxygen free 1 to 10 carbon atom polar organic group and each of the glucose rings has at least one of its OH units substituented to OR' wherein R' is a covalently bound physiologically acceptable noncarbohydrate polar organic group.

10. The compound of claim 9 where R is said polar organic group.

11. The compound of claim 10 wherein R and R' each contains one ore more polar moiety selected from sulfonate, sulfamate, carboxylate, and phosphonate anions, ammonium cations and hydroxyl groups.

12. The compound of claim 11 wherein wherein R and R' are each a 1 to 5 carbon inclusive alkyl terminal sulfonate salt.

13. The compound of claim 12 wherein R and R' are each of the formula

—(CH$_2$)$_n$—SO$_3^-$M$^+$ wherein n is an integer from 2 to 5 inclusive and M$^+$ is a physiologically acceptable alkaline earth metal cation or alkali metal cation.

14. The compound of claim 13 wherein n is 3 and M$^+$ is Na$^+$ or K$^+$.

15. The compound of claim 9 wherein R is hydrogen and R' is a 1 to 5 carbon atom alkylcarboxylate.

16. The compound of claim 15 wherein R' is carboxymethyl group.

17. A steviolmonoside analog compound based on the structure

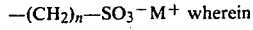

wherein R is hydrogen or a physiologically acceptable noncarbohydrate α-carbon oxygen free 1 to 10 carbon atom polar organic group and the glucose ring has at least one of its OH units substituented to OR' wherein R' is a covalently bound physiologically acceptable noncarbohydrate polar organic group.

18. The compound of claim 17 where R is said polar organic group.

19. The compound of claim 18 wherein R and R' each contains one or more polar moiety selected from sulfonate, sulfamate, carboxylate, and phosphonate anions, ammonium cations and hydroxyl groups.

20. The compound of claim 19 wherein R and R' are each a 1 to 5 carbon inclusive alkyl terminal sulfonate salt.

21. The compound of claim 20 wherein R and R' are of the formula $-(CH_2)_n-SO_3^-M^+$ wherein n is an integer from 2 to 5 inclusive and $M^+$ is a physiologically acceptable alkaline earth metal cation or alkali metal cation.

22. The compound of claim 21 wherein n is 3 and $M^+$ is $Na^+$ or $K^+$.

23. The compound of claim 17 wherein R is hydrogen and R' is a 1 to 5 carbon atom alkylcarboxylate.

24. The compound of claim 23 wherein R' is a carboxymethyl group.

* * * * *